(12) United States Patent
Pike (10) Patent No.: US 10,512,726 B2
(45) Date of Patent: Dec. 24, 2019

(54) CARPULE RETENTIVE SLEEVE WITH INTERNAL STOPPER RETAINER FOR ASPIRATING SYRINGE

(71) Applicant: Mark W. Pike, Fayetteville, NC (US)

(72) Inventor: Mark W. Pike, Fayetteville, NC (US)

( * ) Notice: Subject to any disclaimer, the term of this patent is extended or adjusted under 35 U.S.C. 154(b) by 0 days.

(21) Appl. No.: 15/432,211

(22) Filed: Feb. 14, 2017

(65) Prior Publication Data

US 2018/0228975 A1    Aug. 16, 2018

(51) Int. Cl.
*A61M 5/24* (2006.01)
*A61M 5/28* (2006.01)
*A61M 5/315* (2006.01)

(52) U.S. Cl.
CPC .............. *A61M 5/24* (2013.01); *A61M 5/281* (2013.01); *A61M 5/31505* (2013.01); *A61M 5/31515* (2013.01); *A61M 2005/2414* (2013.01); *A61M 2005/2433* (2013.01)

(58) Field of Classification Search
CPC .... A61M 5/24; A61M 5/281; A61M 5/31515; A61M 2005/2414; A61M 2005/2433; A61M 2005/323; A61M 2005/3231
See application file for complete search history.

(56) References Cited

U.S. PATENT DOCUMENTS

| | | | |
|---|---|---|---|
| 3,640,278 A * | 2/1972 | Friedman | A61M 5/24 604/192 |
| 5,207,646 A * | 5/1993 | Brunel | A61M 5/24 604/110 |

* cited by examiner

*Primary Examiner* — Rebecca E Eisenberg
*Assistant Examiner* — Tasnim Mehjabin Ahmed
(74) *Attorney, Agent, or Firm* — Nexsen Pruet, PLLC; E. Eric Mills (57) ABSTRACT

A carpule retentive sleeve with internal stopper retainer for use with an aspirating syringe is disclosed. The carpule retentive sleeve includes a tubular body. At one end of the tubular body is a collar and a stopper retaining sleeve. The tubular body, the collar, and the stopper retaining sleeve are hollow members. Accordingly, a channel runs along the entire length of the carpule retentive sleeve. Further, a method is provided of retrofitting a standard aspirating syringe with the presently disclosed carpule retentive sleeve. Further, a method is provided of using the presently disclosed carpule retentive sleeve to retain a stopper inside the anesthetic carpule.

12 Claims, 12 Drawing Sheets

CARPULE RETENTIVE SLEEVE WITH INTERNAL STOPPER RETAINER FOR ASPIRATING SYRINGE

TECHNICAL FIELD

The presently disclosed subject matter relates generally to aspirating syringes and more particularly to a carpule retentive sleeve with internal stopper retainer for use with an aspirating syringe.

BACKGROUND

A number of instruments, materials, and equipment are used in restorative, endodontic, prosthetic, orthodontic, surgical, and cosmetic dental procedures. One such instrument is an aspirating syringe (also called a dental syringe or local anesthetic syringe). The aspirating syringe is used in dentistry to inject a local anesthetic. The aspirating syringe differs from most syringes in that it is designed to inject anesthetic from a single-use disposable carpule. The parts of an aspirating syringe consist of a threaded tip where the needle attaches, a barrel where the carpule is placed, a syringe rod (or plunger) with a harpoon attached that embeds itself into the silicone rubber stopper of the carpule, a finger grip, and a thumb ring. The harpoon allows the dentist to aspirate (draw back) the injection site to see if the needle tip is located in a blood vessel before injecting the anesthetic solution. Once the harpoon is engaged into the silicone rubber stopper of the anesthetic carpule, the dentist can apply inward or outward pressure on the stopper by exerting pressure on the thumb ring. Pulling the thumb ring outward also pulls the plunger outward, producing an aspirating effect; whereas pushing inward forces the anesthetic solution through the needle.

One problem of aspirating syringes is that sometimes the stopper gets stuck on the harpoon and pulls out of the carpule when removing the carpule from the syringe. This complicates the need to change the carpule when multiple injections are needed, and the removal of the carpule before sterilizations procedures. The clinician risks injury from the sharp harpoon as one tries to pry the stopper from the harpoon within the syringe barrel. One approach to solving this problem has been to reduce the number and/or size of the barbs on the syringe rod harpoon. However, this sometimes causes difficulty in aspiration due to the rod disengaging from the stopper and only reduces the incident.

SUMMARY

A carpule retentive sleeve with internal stopper retainer for use with an aspirating syringe is disclosed.

The carpule retentive sleeve can include a tubular body provided with a collar disposed at a distal end of the tubular body and a stopper retaining sleeve positioned at a distal end of the collar and sized to fit into a lumen of the carpule at a proximal end of the carpule for preventing a stopper in the lumen of the carpule from being retracted out of the lumen, wherein the tubular body, the collar and the stopper retaining sleeve are hollow, forming a channel through the length of the carpule retentive sleeve.

The collar can have a greater outside diameter than the tubular body. The stopper retaining sleeve can have a smaller outside diameter than the collar. The length of the tubular body can be greater than the length of the stopper retaining sleeve.

The carpule retentive sleeve can further include a stop ring provided at an interface of the tubular body and the collar. The stop ring can have a greater outside diameter than the collar. The stop ring can have an outside diameter at least as large as an outside diameter of a barrel of the aspirating syringe, such that the stop ring stops distal motion of the aspirating syringe motion when the stop ring hits the barrel.

The carpule retentive sleeve can further include a chamfer disposed around the distal end of the collar. The chamfer can be sloped to expand in diameter towards the collar. The chamfer can be configured to self-align the carpule retentive sleeve with the carpule.

The carpule retentive sleeve can further include a groove at a proximal end of the tubular body, opposite the stopper retaining sleeve. The groove can extend around the entirety of the outer circumference of the tubular body. The groove can be adapted to receive a clip.

A method of using a carpule retentive sleeve with an aspirating syringe and a carpule is also disclosed. The method can include providing a carpule retentive sleeve to the aspirating syringe, the carpule retentive sleeve comprising a tubular body provided with a collar disposed at a distal end of the tubular body, and a stopper retaining sleeve positioned at a distal end of the collar and sized to fit into a lumen of the carpule at a proximal end of the carpule for preventing a stopper in the lumen of the carpule from being retracted out of the lumen, wherein the tubular body, the collar and the stopper retaining sleeve are hollow, forming a channel through the length of the carpule retentive sleeve. The method can further include installing the carpule within a barrel of the aspirating syringe such that the carpule is engaged on a proximal end by the stopper retaining sleeve; engaging a harpoon of the aspirating syringe with a stopper of the carpule; using the aspirating syringe to perform at least one of injecting at and aspirating from an injection site; withdrawing the harpoon from the stopper while the stopper retaining sleeve retains the stopper inside the lumen of the carpule; disengaging the carpule from the carpule retentive sleeve; and removing the carpule from the barrel with the stopper still located within the lumen of the carpule.

The method of installing the carpule within the barrel can also include disposing the stopper retaining sleeve into a lumen of the carpule.

The method can also include stopping distal motion of the aspirating syringe during injecting using a stop ring provided at an interface of the tubular body and the collar.

The method can also include self-aligning the carpule retentive sleeve with the carpule using a chamfer disposed around the distal end of the collar.

A method of using a carpule retentive sleeve to retrofit an aspirating syringe is also disclosed. The method can include providing a carpule retentive sleeve to the aspirating syringe, the carpule retentive sleeve comprising a tubular body provided with a collar disposed at a distal end of the tubular body, and a stopper retaining sleeve positioned at a distal end of the collar and sized to fit into a lumen of the carpule at a proximal end of the carpule for preventing a stopper in the lumen of the carpule from being retracted out of the lumen, wherein the tubular body, the collar and the stopper retaining sleeve are hollow, forming a channel through the length of the carpule retentive sleeve. The method can further include removing a barrel of the aspirating syringe; removing a standard carpule sleeve which is being replaced and a spring; placing the spring on the carpule retentive sleeve; inserting a syringe rod of the aspirating syringe through the carpule retentive sleeve; inserting a proximal end of the syringe rod through a finger grip assembly of the aspirating syringe; pulling back the syringe rod through the carpule retentive sleeve and reattaching a barrel to the finger grip assembly; and releasing the syringe rod.

The method can also include removing a thumb ring from a proximal end of the syringe rod; and removing the syringe rod from the figure grip assembly after removing the barrel of the aspirating syringe and before removing the standard carpule sleeve.

BRIEF DESCRIPTION OF THE DRAWINGS

Having thus described the presently disclosed subject matter in general terms, reference will now be made to the accompanying Drawings, which are not necessarily drawn to scale, and wherein:

DETAILED DESCRIPTION

The presently disclosed subject matter now will be described more fully hereinafter with reference to the accompanying Drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides a carpule retentive sleeve with internal stopper retainer for use with an aspirating syringe. The carpule retentive sleeve includes a tubular body. At one end of the tubular body is a collar and a stopper retaining sleeve. The tubular body of the carpule retentive sleeve engages with the finger grip portion of the aspirating syringe, while the stopper retaining sleeve engages with the proximal end of the anesthetic carpule that is in the barrel of the aspirating syringe.

Further, a method is provided of retrofitting a standard aspirating syringe with the presently disclosed carpule retentive sleeve. Additionally, a method is provided of using the presently disclosed carpule retentive sleeve to retain a stopper inside the anesthetic carpule.

An aspect of the presently disclosed carpule retentive sleeve and methods is that they can be used to ensure that the stopper (e.g., a silicone rubber stopper) is retained inside the anesthetic carpule when the syringe rod harpoon is disengaged from the stopper and withdrawn from the carpule.

It should also be understood that as used herein, "proximal" or "proximally" means closest to an attending medical professional (e.g. performing a procedure where the aspirating syringe is being held) or in a direction towards the outside of the patient's body and "distal" or "distally" means closest to the patient's mouth or in direction moving further inside the patient's body.

Figure 1:
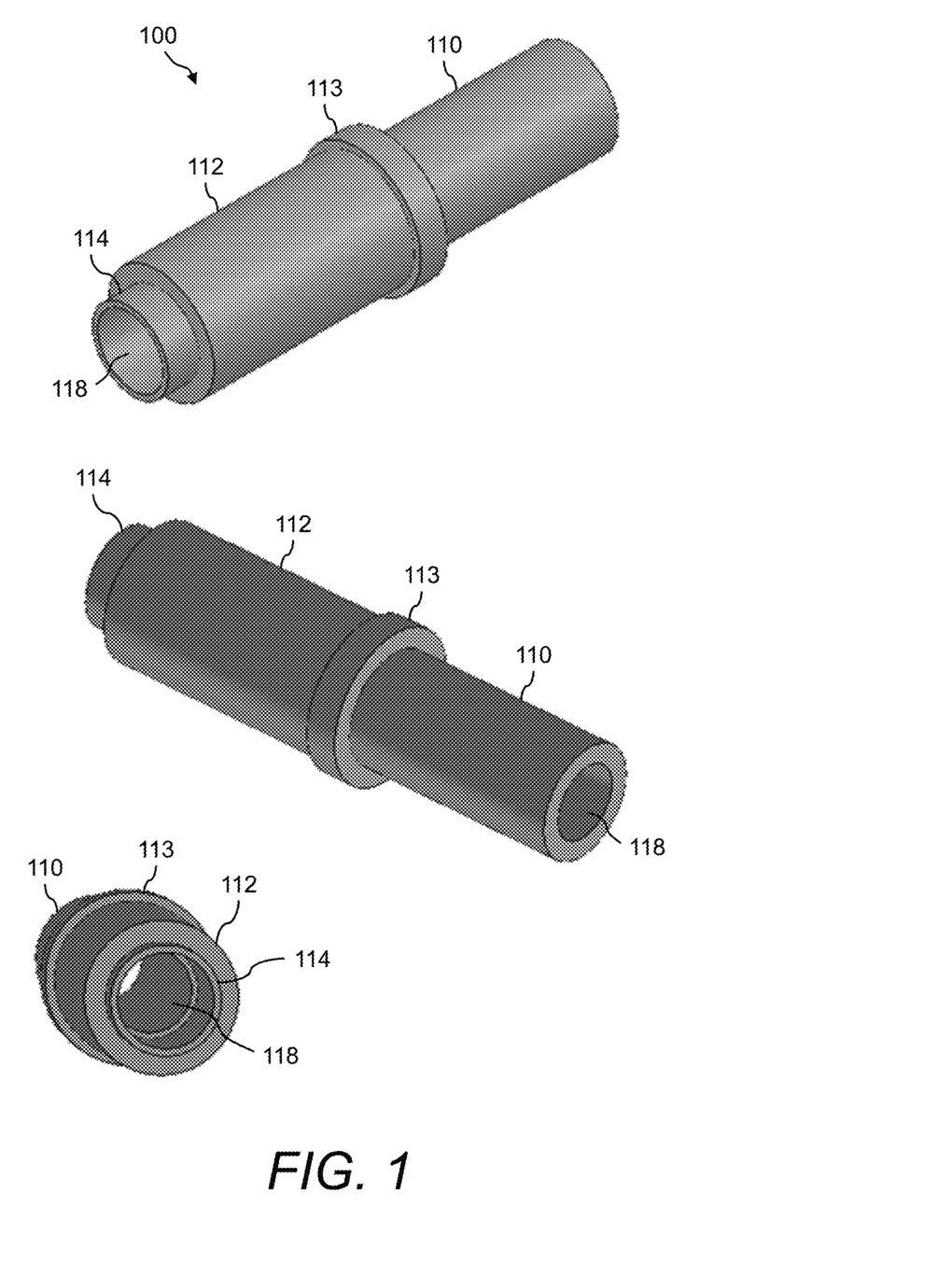
FIG. 1 illustrates perspective views of an example of the presently disclosed carpule retentive sleeve for use with an aspirating syringe.
Figure 2:
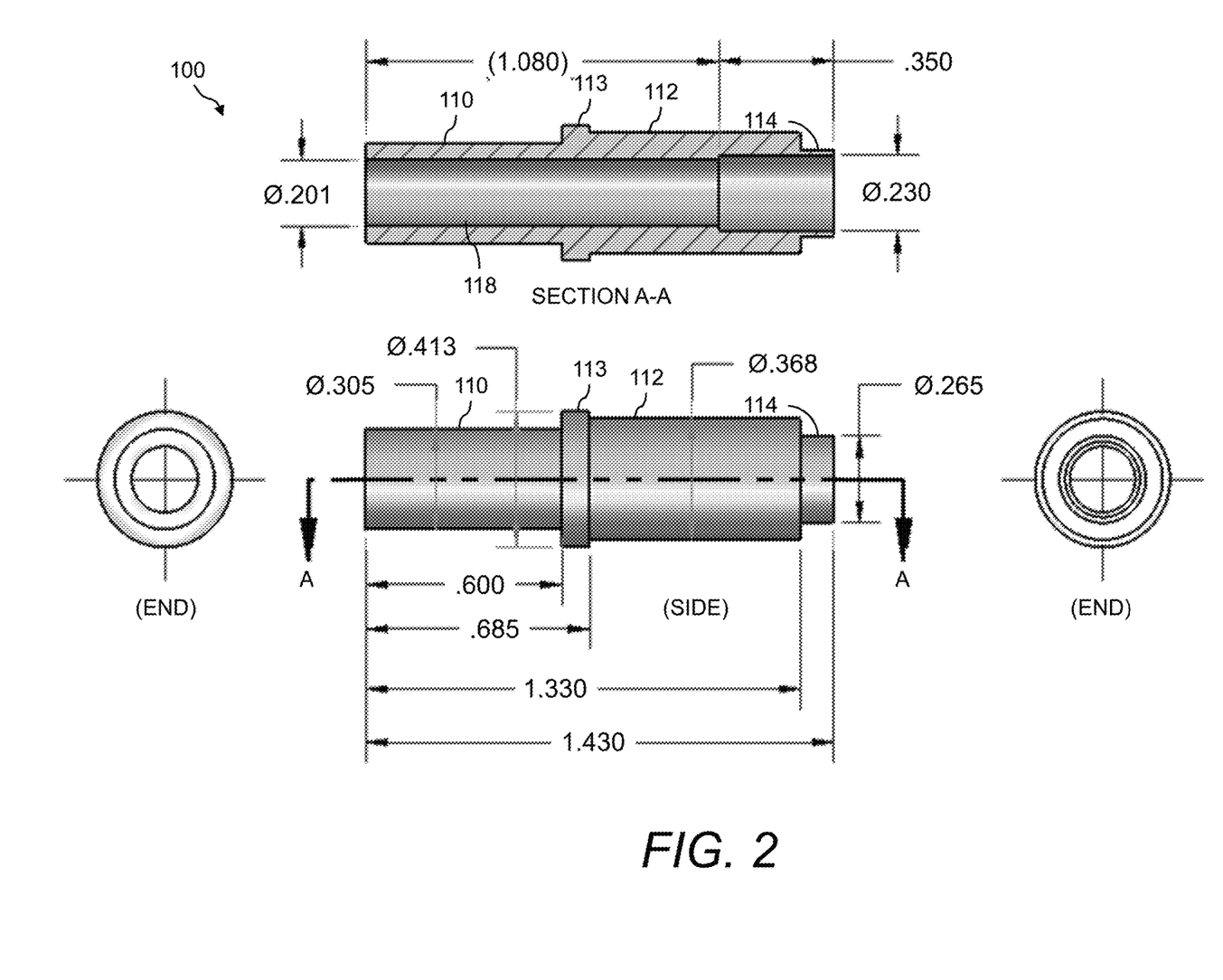
FIG. 2 shows a side view, end views, and a cross-sectional view that show more details of the carpule retentive sleeve shown in FIG. 1.

Referring now to FIG. 1 are perspective views of an example of the presently disclosed carpule retentive sleeve 100 for use with an aspirating syringe. The carpule retentive sleeve 100 includes a tubular body 110. Further, a collar 112 and a stopper retaining sleeve 114 is arranged at one end of tubular body 110. Further, a stop ring feature 113 is provided at the interface of tubular body 110 and collar 112. Tubular body 110, collar 112, and stopper retaining sleeve 114 are hollow members. Accordingly, a channel 118 runs along the entire length of carpule retentive sleeve 100. FIG. 2 shows a side view, end views, and a cross-sectional view that show more details of the carpule retentive sleeve 100 shown in FIG. 1. The cross-sectional view shown in FIG. 2 is taken along line A-A of the side view in FIG. 2. The example dimensions shown in FIG. 2 are in inches. Carpule retentive sleeve 100 can be sized to fit into any standard aspirating syringe and to mate with any standard anesthetic carpule.

FIG. 2 shows that the inside diameters and outside diameters of tubular body 110 and stopper retaining sleeve 114 differ slightly, while the length of tubular body 110 (e.g., 0.6 inches) is significantly greater than the length of stopper retaining sleeve 114 (e.g., 0.1 inches). Further, the diameter of channel 118 in the tubular body 110-portion can be slightly different than the diameter in the collar 112-portion of carpule retentive sleeve 100. In one example, the diameter of channel 118 in the tubular body 110-portion is about 0.201 inches, while the diameter of channel 118 in the collar 112-portion is about 0.230 inches. The presently disclosed carpule retentive sleeve 100 can be formed, for example, of molded plastic, glass, stainless steel, or other suitable material.

Figure 3A:
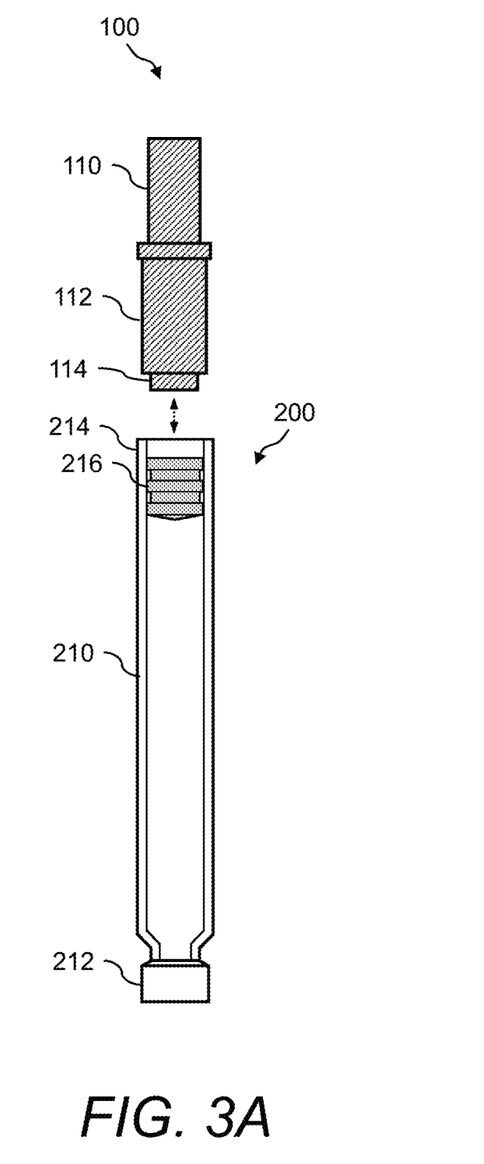
FIG. 3A and FIG. 3B show side views of the presently disclosed carpule retentive sleeve in relation to an anesthetic carpule and a process of engaging the carpule retentive sleeve with the carpule.
Figure 3B:
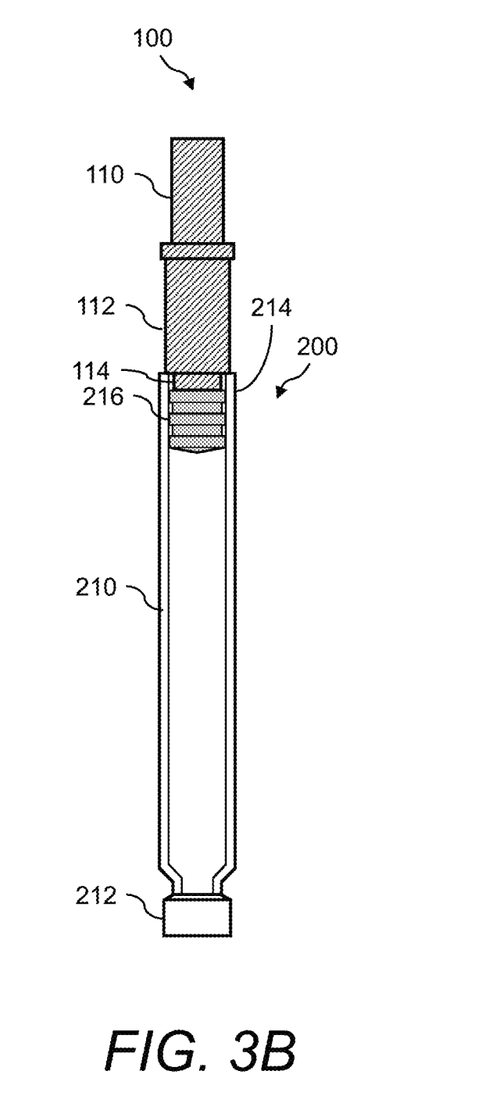

Referring now to FIG. 3A and FIG. 3B are side views of the presently disclosed carpule retentive sleeve 100 in relation to an anesthetic carpule 200 and a process of engaging carpule retentive sleeve 100 with carpule 200. Carpule 200 can be a standard single-use disposable carpule. Carpule 200 includes a cylinder-shaped vessel 210 for holding a quantity of, for example, anesthesia (not shown). Cylinder-shaped vessel 210 has a distal end 212, which is the end of vessel 210 to which a needle (not shown) attaches. Cylinder-shaped vessel 210 has a proximal end 214, which is the end of vessel 210 that receives the plunger of the aspirating syringe (see FIG. 4). A stopper 216 is slideably installed within vessel 210. Stopper 216 can be, for example, a silicone rubber stopper. Stopper 216 is used to push the anesthesia out of carpule 200.

When using carpule retentive sleeve 100, stopper retaining sleeve 114 of carpule retentive sleeve 100 is oriented toward proximal end 214 of vessel 210 (FIG. 3A). Then, stopper retaining sleeve 114 of carpule retentive sleeve 100 is fitted into proximal end 214 of vessel 210 (FIG. 3B).

Figure 4:
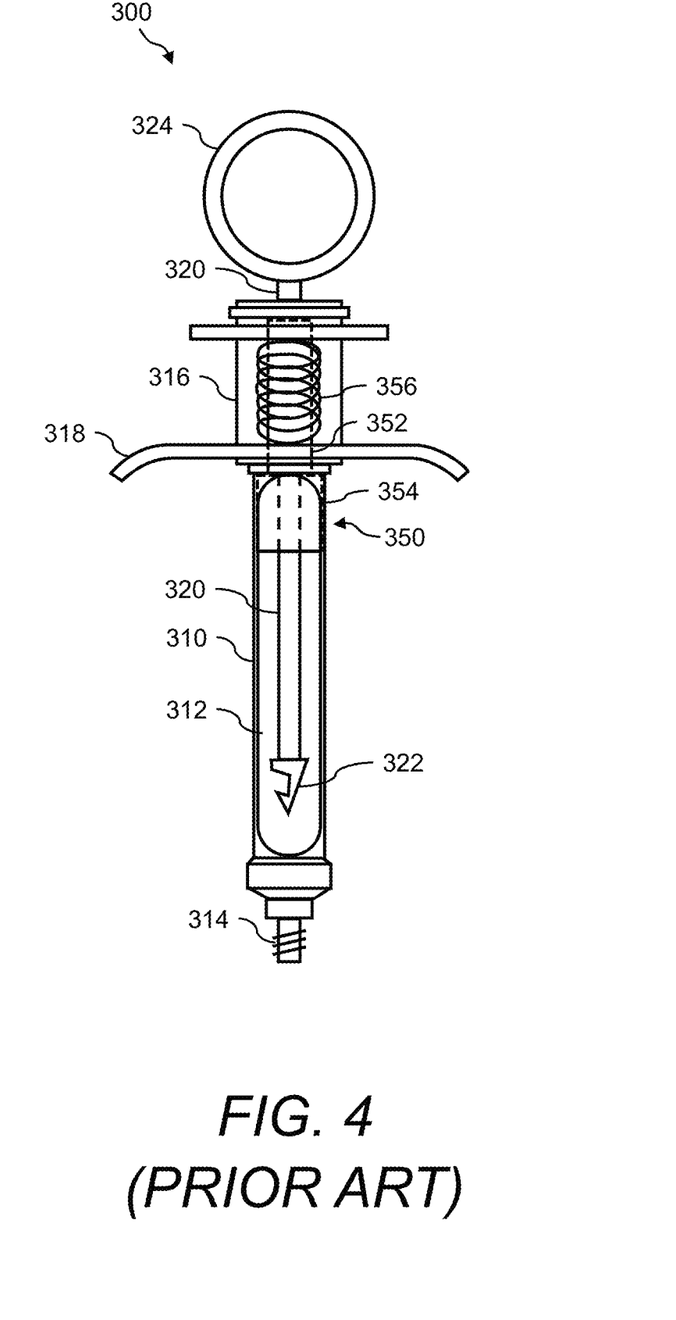
FIG. 4 illustrates a side view of an example of an aspirating syringe that can be retrofitted with the presently disclosed carpule retentive sleeve can be used.

Referring now to FIG. 4 is a side view of an example of an aspirating syringe 300 that can be retrofitted with the presently disclosed carpule retentive sleeve 100. Aspirating syringe 300 is exemplary of any standard aspirating syringe that includes a standard external carpule retentive sleeve 350 that can be replaced with the presently disclosed carpule retentive sleeve 100. The external carpule retentive sleeve 350 is a hollow tubular member that fits against the top of the carpule (e.g., carpule 200). The external carpule retentive sleeve 350 is termed "external" because no portion of carpule retentive sleeve is fitted internal to the carpule (e.g., carpule 200).

Aspirating syringe 300 generally includes a barrel 310 in which the carpule is placed. Namely, an opening (or slot) 312 along one side of barrel 310 allows the carpule (e.g., carpule 200) to be loaded into barrel 310. Opening 312 also allows the user to visually monitor the anesthetic level within the carpule. A threaded tip 314 to which the needle (not shown) attaches is at the distal end of barrel 310. A finger grip assembly 316 that has a finger bar 318 is arranged at the proximal end of barrel 310. A syringe rod (or plunger) 320 passes through external carpule retentive sleeve 350 and a spring 356. External carpule retentive sleeve 350 and spring 356 are arranged within finger grip assembly 316, while syringe rod 320 is slideably arranged within barrel 310. External carpule retentive sleeve 350 includes a tubular body 352 and a collar 354, wherein collar 354 is oriented toward and in the barrel 310 of aspirating syringe 300. A barbed harpoon 322 is provided at the distal end of syringe rod 320. A thumb ring 324 is provided at the proximal end of syringe rod 320.

When, for example, carpule 200 is installed in barrel 310 of aspirating syringe 300, collar 354 of external carpule retentive sleeve 350 abuts against the end of carpule 200. In so doing, the spring-loaded external carpule retentive sleeve 350 applies force against carpule 200. When in use, barbed harpoon 322 embeds into the silicone rubber stopper of the carpule, such as stopper 216 of carpule 200. Namely, barbed harpoon 322 allows the dentist to aspirate (draw back) when the needle is inserted, to make sure the needle tip is not located in a blood vessel before injecting the anesthetic solution. Once barbed harpoon 322 is engaged into the stopper (e.g., silicone rubber stopper) of the anesthetic carpule (see FIG. 7A, FIG. 7B, FIG. 7C), the dentist can apply inward or outward pressure on the stopper by exerting pressure on thumb ring 324. Pulling thumb ring 324 outward also pulls the syringe rod 320 outward, producing an aspirating effect; whereas pushing inward forces the anesthetic solution through the needle. The design of the standard external carpule retentive sleeve, such as external carpule retentive sleeve 350, is such that nothing prevents the stopper from pulling out of carpule 200 and up into the standard external carpule retentive sleeve during aspiration.

Figure 5:
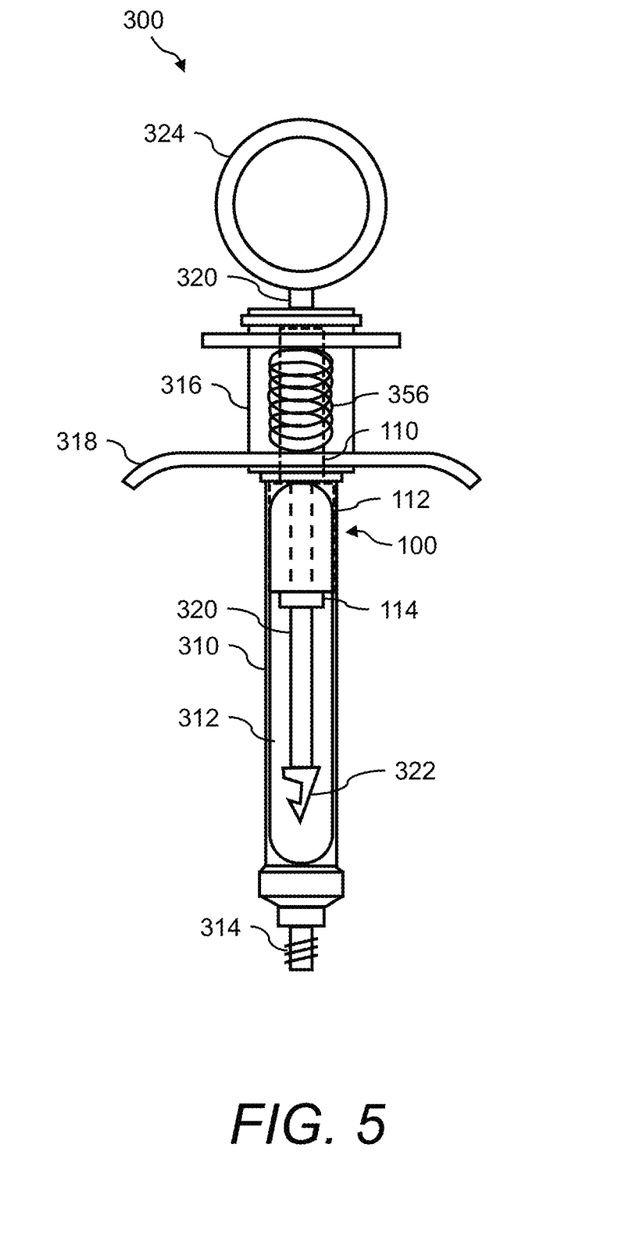
FIG. 5 illustrates a side view of an example of a retrofitted aspirating syringe that includes the presently disclosed carpule retentive sleeve installed therein.

The standard aspirating syringe 300 can be retrofitted with the presently disclosed carpule retentive sleeve 100. Namely, the standard external carpule retentive sleeve 350 of aspirating syringe 300 can be replaced with carpule retentive sleeve 100 as shown, for example, in FIG. 5. FIG. 5 shows carpule retentive sleeve 100 arranged along with spring 356 within finger grip assembly 316 of aspirating syringe 300. Spring 356 is arranged around tubular body 110-portion of carpule retentive sleeve 100 and collar 112 is oriented toward and in the barrel 310 of aspirating syringe 300. Accordingly, FIG. 5 shows a retrofitted aspirating syringe 300.

Figure 6:
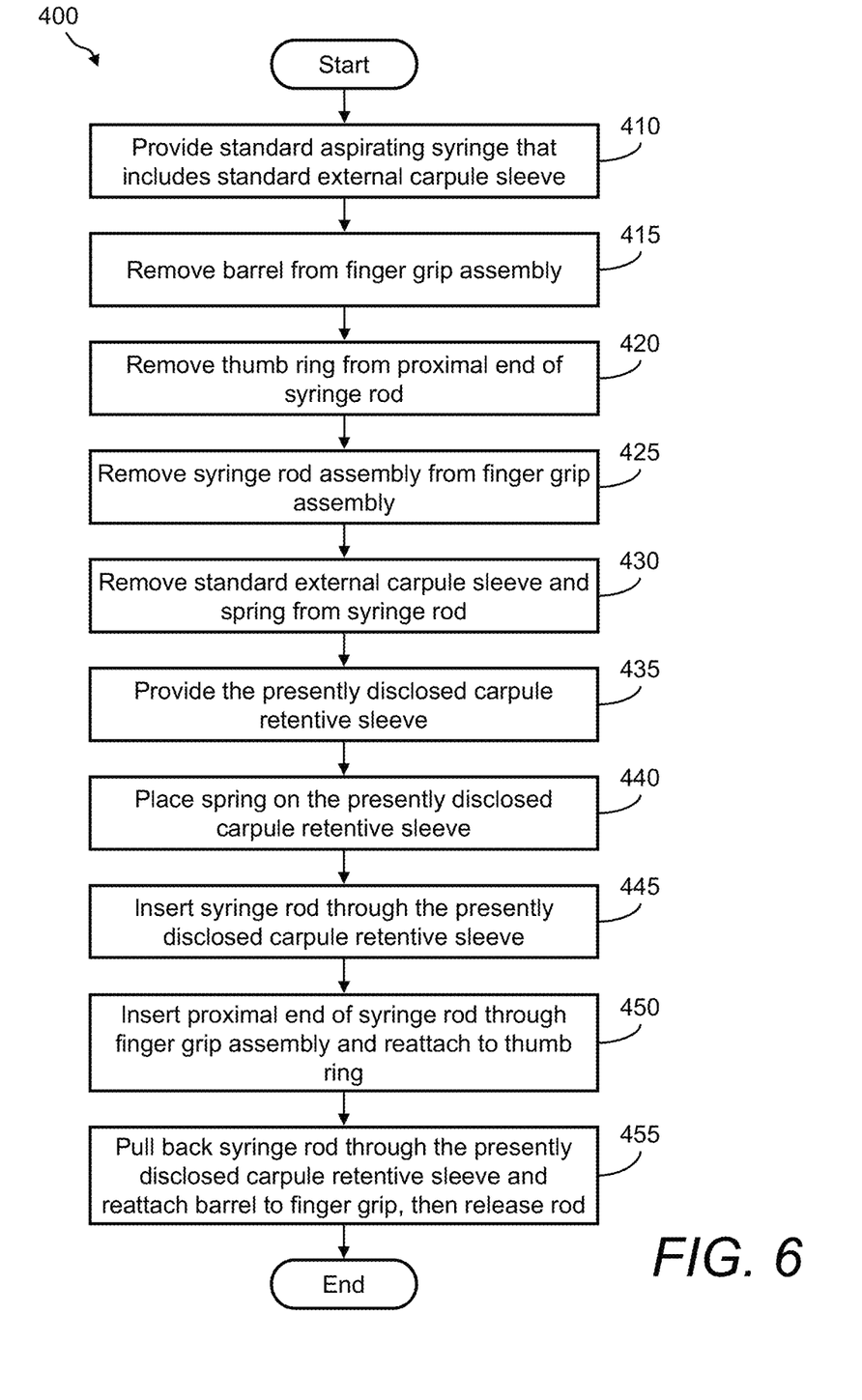
FIG. 6 illustrates a flow diagram of an example of a method of retrofitting a standard aspirating syringe with the presently disclosed carpule retentive sleeve.

FIG. 6 illustrates a flow diagram of an example of a method 400 of retrofitting a standard aspirating syringe with the presently disclosed carpule retentive sleeve 100. Method 400 may include, but is not limited to, the following steps.

At a step 410, a standard aspirating syringe, which includes a standard external carpule sleeve, is provided. For example, the standard aspirating syringe 300 shown in FIG. 4 may be provided, wherein aspirating syringe 300 includes the standard external carpule retentive sleeve 350.

At a step 415, the barrel is removed from the finger grip assembly. For example, in aspirating syringe 300 of FIG. 4, barrel 310 is removed, for example, by unscrewing barrel 310 from the base of finger grip assembly 316.

At a step 420, the thumb ring is removed from the proximal end of the syringe rod. For example, in aspirating syringe 300 of FIG. 4, thumb ring 324 is removed, for example, by unscrewing thumb ring 324 from the proximal end of syringe rod 320.

At a step 425, the syringe rod assembly is removed from the finger grip assembly. For example, in aspirating syringe 300 of FIG. 4, syringe rod 320 along with external carpule retentive sleeve 350 and spring 356 is pulled through and removed from finger grip assembly 316.

At a step 430, the standard external carpule sleeve and the spring is removed from the syringe rod. For example, in aspirating syringe 300 of FIG. 4, external carpule retentive sleeve 350 and spring 356 are slid off of and removed from syringe rod 320.

At a step 435, the presently disclosed carpule retentive sleeve 100 is provided. For example, the carpule retentive sleeve 100 described with reference to FIG. 1, FIG. 2, FIG. 3A, and FIG. 3B is provided.

At a step 440, the spring is placed on the presently disclosed carpule retentive sleeve 100. For example, spring 356 of aspirating syringe 300 of FIG. 5 is placed on the tubular body 110-portion of carpule retentive sleeve 100.

At a step 445, the syringe rod is inserted through the presently disclosed carpule retentive sleeve 100. For example, the proximal end of syringe rod 320 of aspirating syringe 300 of FIG. 5 is inserted through channel 118 of carpule retentive sleeve 100.

At a step 450, the proximal end of the syringe rod is inserted through the finger grip assembly and the thumb ring is reattached. For example, with carpule retentive sleeve 100 and spring 356 arranged on syringe rod 320, the proximal end of syringe rod 320 of aspirating syringe 300 of FIG. 5 is inserted through finger grip assembly 316. Then, thumb ring 324 is reattached, for example, by screwing thumb ring 324 to the proximal end of syringe rod 320.

At a step 455, the syringe rod is pulled back through the presently disclosed carpule retentive sleeve 100, which is spring-loaded, and then the barrel is reattached to the finger grip assembly. Then, the syringe rod is released. For example, in retrofitted aspirating syringe 300 of FIG. 5, syringe rod 320 is pulled back through carpule retentive sleeve 100, which is spring-loaded, and then barrel 310 is reattached to finger grip assembly 316. For example, barrel 310 can be screwed to the base of finger grip assembly 316. Then, syringe rod 320 can be released.

At the end of method 400, the retrofitted aspirating syringe 300, which includes the presently disclosed carpule retentive sleeve 100, is ready to receive the carpule (e.g., carpule 200).

In other embodiments, instead of retrofitting an existing aspirating syringe, the presently disclosed carpule retentive sleeve 100 is installed in the aspirating syringe at the time of manufacture.

Figure 7A:
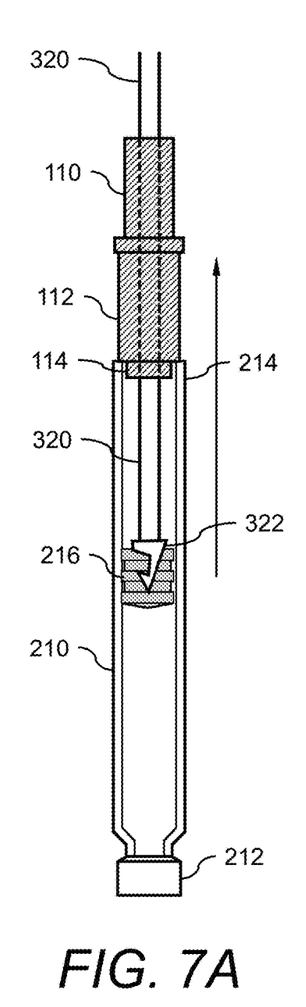
FIG. 7A, FIG. 7B, and FIG. 7C show an example of a process of using the presently disclosed carpule retentive sleeve to ensure that the stopper is retained inside the anesthetic carpule.
Figure 7B:
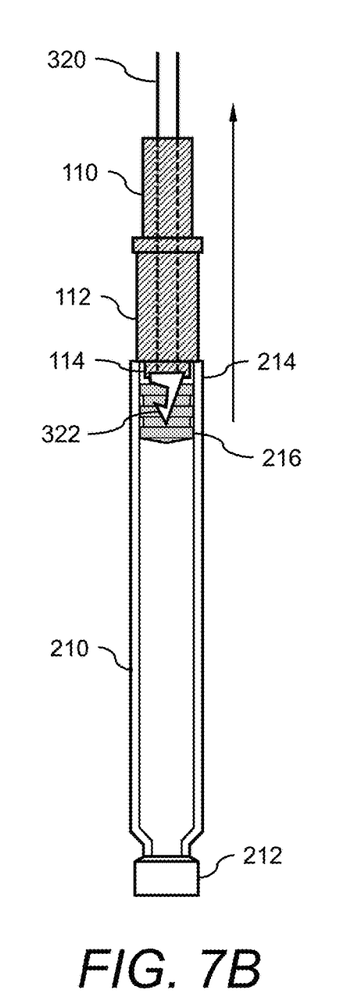
Figure 7C:
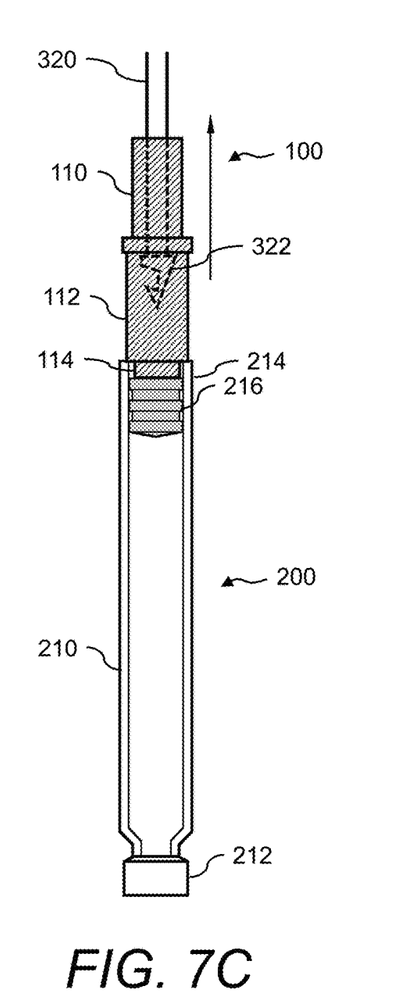

Referring now to FIG. 7A, FIG. 7B, and FIG. 7C is an example of a process of using the presently disclosed carpule retentive sleeve 100 to ensure that stopper 216 is retained inside the anesthetic carpule. For example, FIG. 7A, FIG. 7B, and FIG. 7C show a process of using carpule retentive sleeve 100 to ensure that stopper 216 is retained inside vessel 210 of carpule 200. For simplicity, FIG. 7A, FIG. 7B, and FIG. 7C show only the syringe rod 320 and barbed harpoon 322 of aspirating syringe 300. In particular, FIG. 7A, FIG. 7B, and FIG. 7C show barbed harpoon 322 embedded into stopper 216 of carpule 200.

Once the use of aspirating syringe 300 is completed, the syringe rod 320 with barbed harpoon 322 is drawn back to disengage barbed harpoon 322 from stopper 216 of carpule 200. Then, carpule 200 can be removed from the aspirating syringe (e.g., aspirating syringe 300). For example, FIG. 7A shows the process of withdrawing the syringe rod 320 with barbed harpoon 322, thereby pulling stopper 216 toward proximal end 214 of carpule 200. FIG. 7B shows stopper 216 stopped against stopper retaining sleeve 114 of carpule retentive sleeve 100 and with barbed harpoon 322 of aspirating syringe 300 still embedded into stopper 216 of carpule 200. FIG. 7C shows barbed harpoon 322 of aspirating syringe 300 withdrawn and disengaged from stopper 216 of carpule 200. All the while, stopper 216 of carpule 200 is held secure against stopper retaining sleeve 114 of carpule retentive sleeve 100, thereby ensuring that stopper 216 is retained inside vessel 210 of carpule 200. That is, by using the presently disclosed carpule retentive sleeve 100, stopper 216 is not allowed to be stuck to barbed harpoon 322 and be pulled out of carpule 200.

Figure 8:
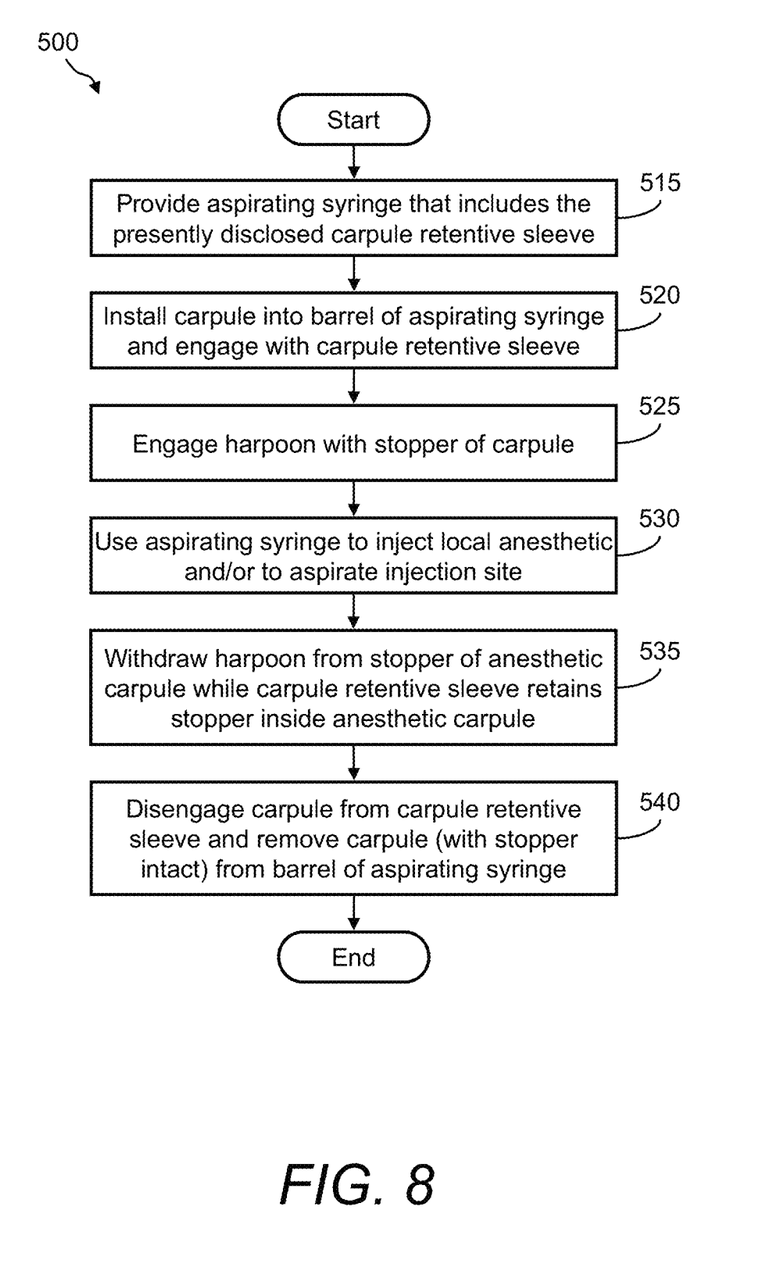
FIG. 8 illustrates a flow diagram of an example of a method of using the presently disclosed carpule retentive sleeve to retain the stopper inside the anesthetic carpule.

Referring now to FIG. 8 is a flow diagram of an example of a method 500 of using the presently disclosed carpule retentive sleeve 100 to retain the stopper inside the anesthetic carpule. Method 500 may include, but is not limited to, the following steps.

At a step 515, an aspirating syringe that includes the presently disclosed carpule retentive sleeve 100 is provided. For example, the retrofitted aspirating syringe 300 shown in FIG. 5 is provided.

At a step 520, the carpule is installed into the barrel of the aspirating syringe and carpule retentive sleeve 100 is engaged with the carpule. For example, in retrofitted aspirating syringe 300 of FIG. 5, syringe rod 320 is pulled back through carpule retentive sleeve 100, which is spring-loaded. Then, carpule 200 is inserted through opening 312 and loaded into barrel 310. Then, syringe rod 320 is slowly released and stopper retaining sleeve 114 of carpule retentive sleeve 100 is mated to carpule 200 as shown in FIG. 3B and also shown in FIG. 7A, FIG. 7B, and FIG. 7C.

At a step 525, the harpoon is engaged with the stopper of the carpule. For example, barbed harpoon 322 of aspirating syringe 300 is embedded into stopper 216 of carpule 200 as shown, for example, in FIG. 7A, FIG. 7B, and FIG. 7C.

At a step 530, the aspirating syringe is used to inject local anesthetic and to aspirate injection site periodically throughout the injection procedure. For example, aspirating syringe 300 with carpule retentive sleeve 100 and carpule 200 installed therein is used to inject local anesthetic and/or to aspirate injection site.

At a step 535, the harpoon is withdrawn from the stopper of the anesthetic carpule while carpule retentive sleeve 100 retains the stopper inside the anesthetic carpule. For example, barbed harpoon 322 of aspirating syringe 300 is disengaged from stopper 216 of carpule 200 while stopper retaining sleeve 114 of carpule retentive sleeve 100 holds stopper 216 inside vessel 210 of carpule 200 as shown in FIG. 7C. That is, by using the presently disclosed carpule retentive sleeve 100, stopper 216 is not allowed to be stuck to barbed harpoon 322 and be pulled out of carpule 200.

At a step 540, the carpule is disengaged from carpule retentive sleeve 100 and the carpule (with the stopper intact) is removed from the barrel of the aspirating syringe. For example, syringe rod 320 is fully withdrawn from barrel 310 of aspirating syringe 300. Then, carpule 200 is disengaged from carpule retentive sleeve 100 and carpule 200 (with the stopper 216 intact) is removed from barrel 310 of aspirating syringe 300 (through opening 312).

Figure 9:
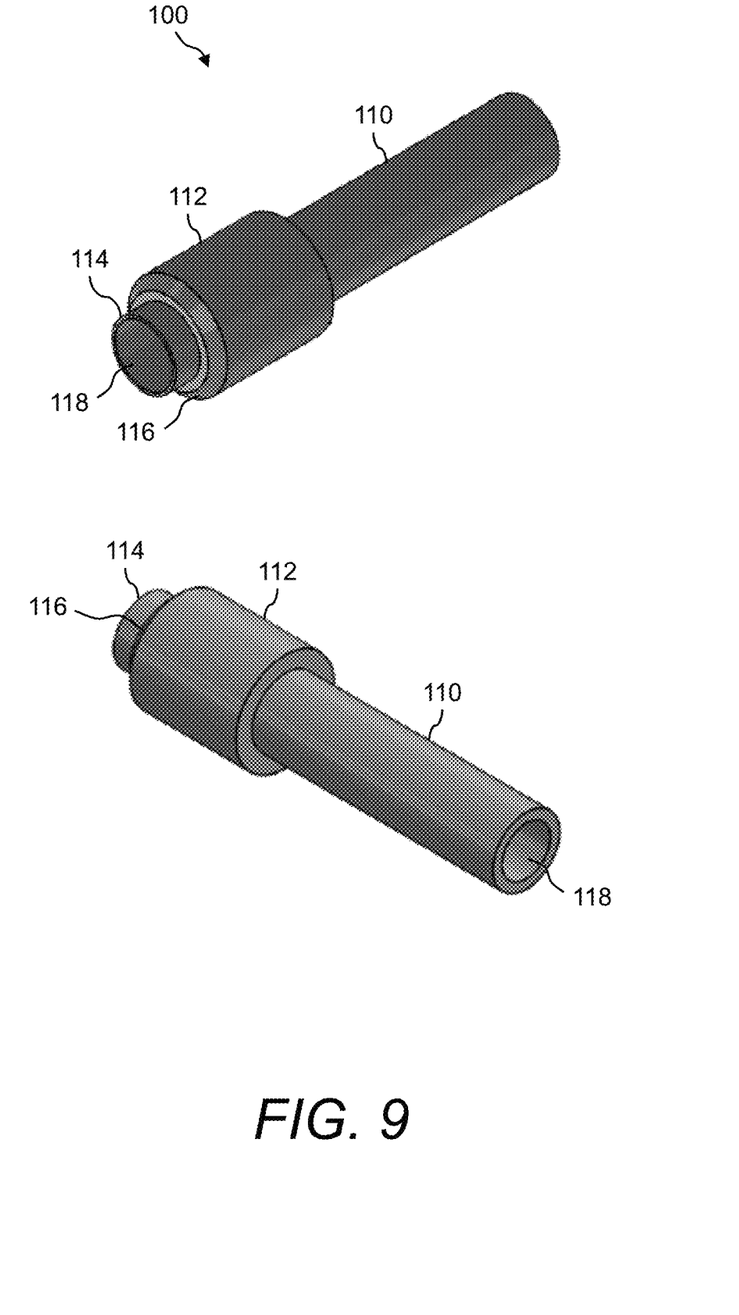
FIG. 9 illustrates perspective views of another example of the presently disclosed carpule retentive sleeve for use with an aspirating syringe.
Figure 10A:
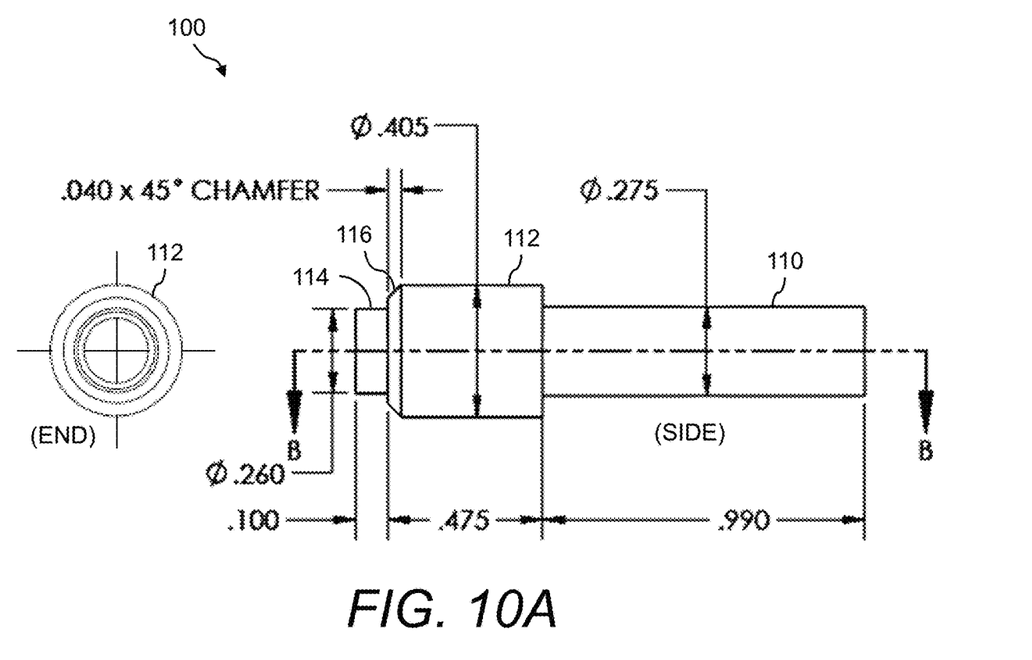
FIG. 10A and FIG. 10B show more details of the carpule retentive sleeve shown in FIG. 9.
Figure 10B:
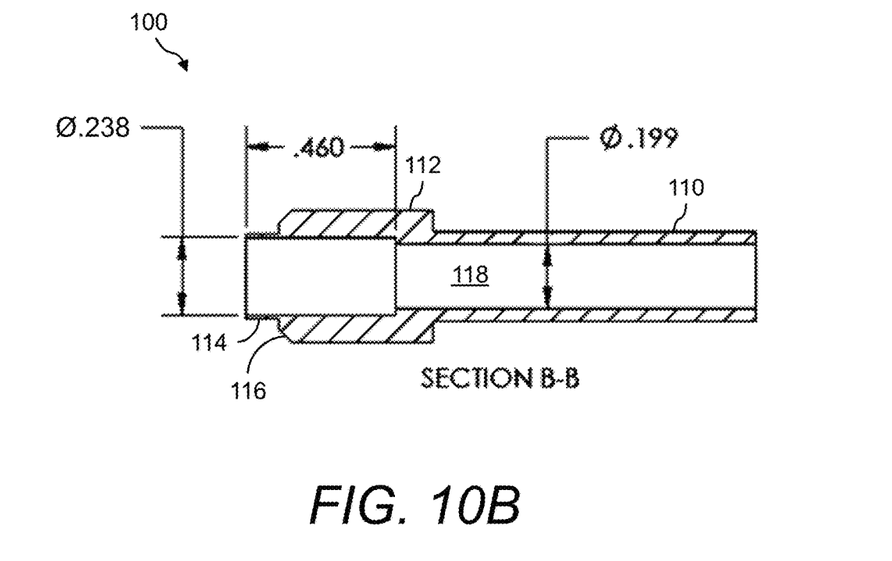

FIG. 9 illustrates perspective views of another example of the presently disclosed carpule retentive sleeve 100 for use with an aspirating syringe. Further, FIG. 10A and FIG. 10B show more details of the carpule retentive sleeve 100 shown in FIG. 9. Namely, FIG. 10A shows a side view and an end view of the carpule retentive sleeve 100 shown in FIG. 9 and FIG. 10B shows a cross-sectional view of the carpule retentive sleeve 100 taken along line B-B of FIG. 10A. The example dimensions shown in FIG. 10A and FIG. 10B are in inches. The carpule retentive sleeve 100 shown in FIG. 9, FIG. 10A, and FIG. 10B is substantially the same as the carpule retentive sleeve 100 shown in FIG. 1 and FIG. 2 except that it further includes a chamfer 116 on the edge of collar 112 that is oriented toward stopper retaining sleeve 114. Further, the stop ring feature 113 is omitted. Chamfer 116 on collar 112 helps to self-align carpule retentive sleeve 100 to proximal end 214 of vessel 210 of carpule 200.

FIG. 10A and FIG. 10B show that the inside diameters and outside diameters of tubular body 110 and stopper retaining sleeve 114 differ slightly, while the length of tubular body 110 (e.g., 0.99 inches) is significantly greater than the length of stopper retaining sleeve 114 (e.g., 0.1 inches). Further, the diameter of channel 118 in the tubular body 110-portion can be slightly different than the diameter in the collar 112-portion of carpule retentive sleeve 100. In one example and referring now to FIG. 10B, the diameter of channel 118 in the tubular body 110-portion is about 0.199 inches, while the diameter of channel 118 in the collar 112-portion is about 0.238 inches.

Figure 11:
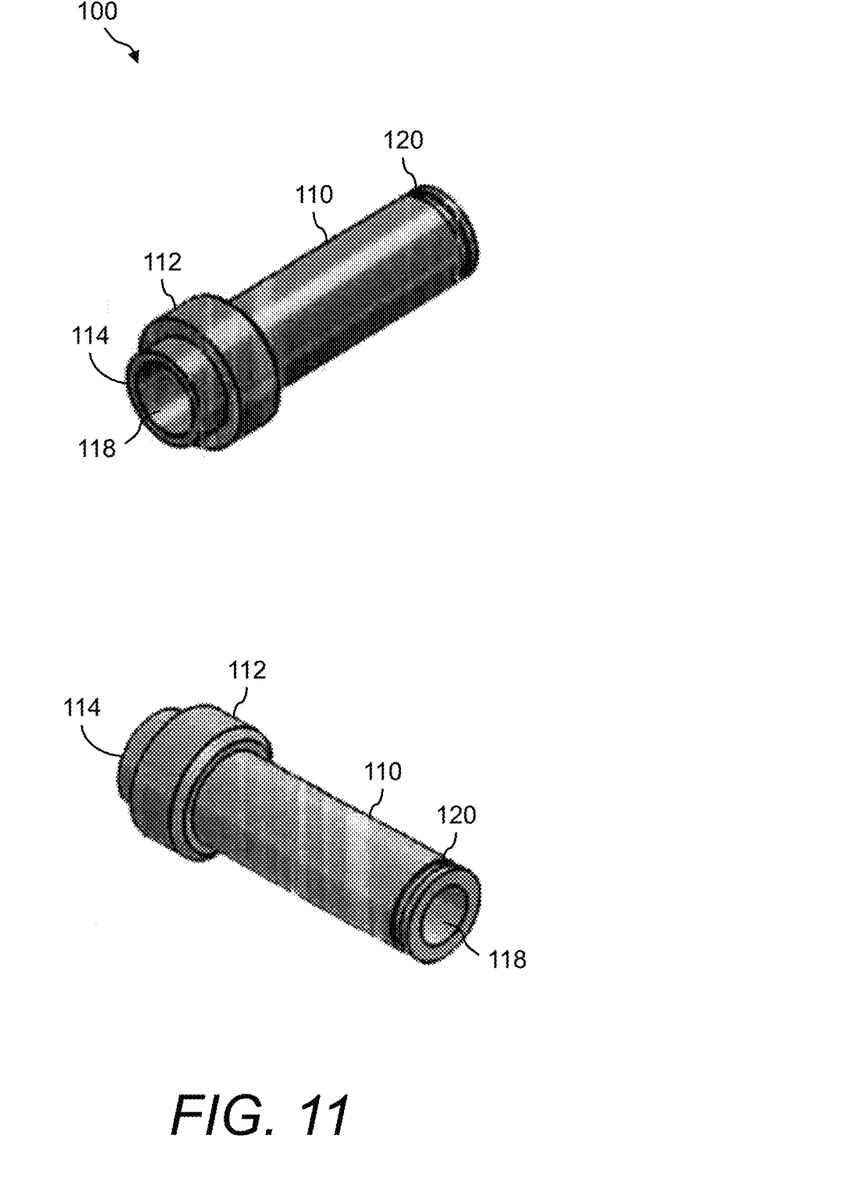
FIG. 11 illustrates perspective views of yet another example of the presently disclosed carpule retentive sleeve for use with an aspirating syringe.
Figure 12A:
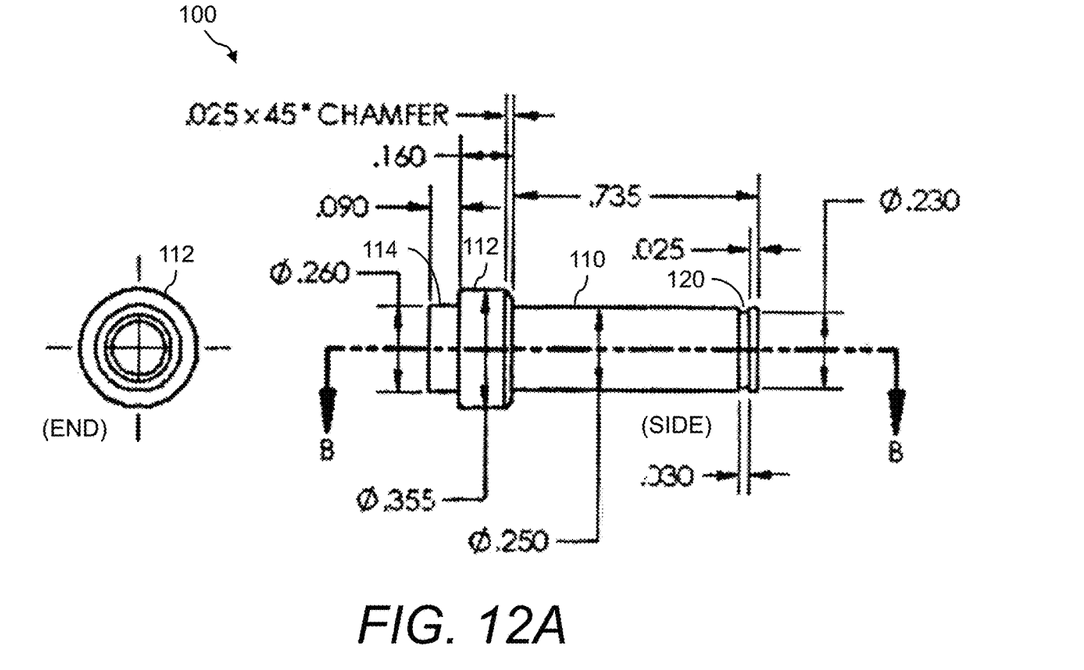
FIG. 12A and FIG. 12B show more details of the carpule retentive sleeve shown in FIG. 11.
Figure 12B:
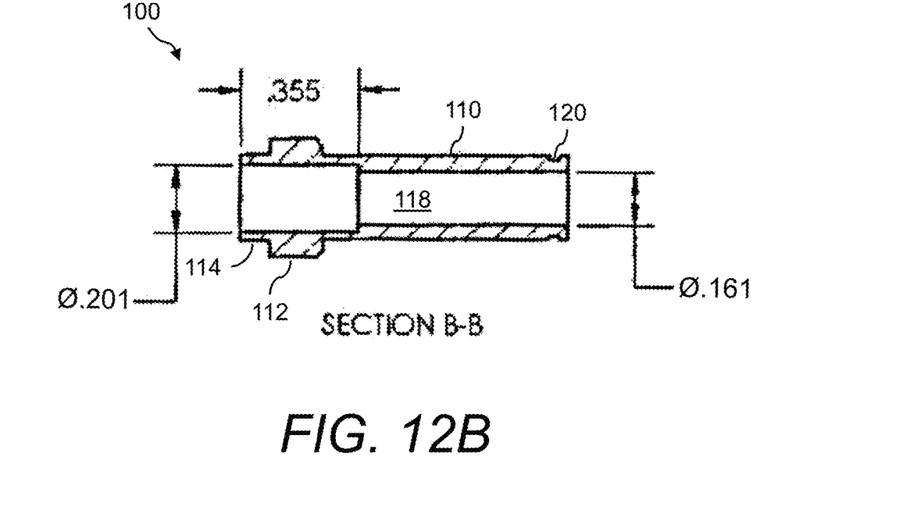

Referring now to FIG. 11 are perspective views of yet another example of the presently disclosed carpule retentive sleeve 100 for use with another style of aspirating syringe. Further, FIG. 12A and FIG. 12B show more details of the carpule retentive sleeve 100 shown in FIG. 11. Namely, FIG. 12A shows a side view and an end view of the carpule retentive sleeve 100 shown in FIG. 11 and FIG. 12B shows a cross-sectional view of the carpule retentive sleeve 100 taken along line B-B of FIG. 12A. The example dimensions shown in FIG. 12A and FIG. 12B are in inches.

The carpule retentive sleeve 100 shown in FIG. 11, FIG. 12A, and FIG. 12B is substantially the same as the carpule retentive sleeve 100 shown in FIG. 9, FIG. 10A, and FIG. 10B except that it further includes a groove 120 at the end of tubular body 110 opposite stopper retaining sleeve 114. Groove 120 is designed to receive a clip (not shown).

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A carpule retentive sleeve for use with an aspirating syringe and a carpule, comprising:
    a tubular body provided with a collar disposed at a distal end of the tubular body; and
    a stopper retaining sleeve positioned at a distal end of the collar and sized to fit into a lumen of the carpule at a proximal end of the carpule for preventing a stopper in the lumen of the carpule from being retracted out of the lumen, the stopper retaining sleeve having a smaller outside diameter than an outside diameter of the collar; herein the tubular body, the collar and the stopper retaining sleeve are hollow, forming a channel through the length of the carpule retentive sleeve, and
    wherein the collar is insertable into a barrel of the aspirating syringe.

2. A carpule retentive sleeve according to claim 1, wherein the collar has a greater outside diameter than the tubular body.

3. A carpule retentive sleeve according to claim 1, wherein the length of the tubular body is greater than the length of the stopper retaining sleeve.

4. A carpule retentive sleeve according to claim 1, further comprising a stop ring provided at an interface of the tubular body and the collar.

5. A carpule retentive sleeve according to claim 1, further comprising a groove at a proximal end of the tubular body, opposite the stopper retaining sleeve.

6. A carpule retentive sleeve according to claim 5, wherein the groove extends around the entirety of the outer circumference of the tubular body.

7. A carpule retentive sleeve according to claim 5, wherein the groove is adapted to receive a clip.

8. A carpule retentive sleeve for use with an aspirating syringe and a carpule, comprising:
    a tubular body provided with a collar disposed at a distal end of the tubular body;
    a stopper retaining sleeve positioned at a distal end of the collar and sized to fit into a lumen of the carpule at a proximal end of the carpule for preventing a stopper in the lumen of the carpule from being retracted out of the lumen, the stopper retaining sleeve having a smaller outside diameter than an outside diameter of the collar; and
    a stop ring provided at an interface of the tubular body and the collar;
    wherein the tubular body, the collar and the stopper retaining sleeve are hollow, forming a channel through the length of the carpule retentive sleeve, and
    wherein the stop ring has a greater outside diameter than the collar.

9. A carpule retentive sleeve according to claim 8, wherein the stop ring has an outside diameter at least as large as an outside diameter of a barrel of the aspirating syringe.

10. A carpule retentive sleeve for use with an aspirating syringe and a carpule, comprising:
    a tubular body provided with a collar disposed at a distal end of the tubular body;
    a stopper retaining sleeve positioned at a distal end of the collar and sized to fit into a lumen of the carpule at a proximal end of the carpule for preventing a stopper in the lumen of the carpule from being retracted out of the lumen, the stopper retaining sleeve having a smaller outside diameter than an outside diameter of the collar; and
    a chamfer disposed around the distal end of the collar;
    wherein the tubular body, the collar and the stopper retaining sleeve are hollow, forming a channel through the length of the carpule retentive sleeve.

11. A carpule retentive sleeve according to claim 10, wherein the chamfer is sloped to expand in diameter towards the collar.

12. A carpule retentive sleeve according to claim 10, wherein the chamfer is configured to self-align the carpule retentive sleeve with the carpule.

\* \* \* \* \*